(12) United States Patent
Mosler

(10) Patent No.: US 8,317,876 B2
(45) Date of Patent: *Nov. 27, 2012

(54) ARTIFICIAL FOOT

(75) Inventor: Lüder Mosler, Duderstadt (DE)

(73) Assignee: Otto Bock HealthCare GmbH, Duderstadt (DE)

( * ) Notice: Subject to any disclaimer, the term of this patent is extended or adjusted under 35 U.S.C. 154(b) by 168 days.

This patent is subject to a terminal disclaimer.

(21) Appl. No.: 12/158,813

(22) PCT Filed: Dec. 14, 2006

(86) PCT No.: PCT/DE2006/002241
§ 371 (c)(1),
(2), (4) Date: Jun. 23, 2008

(87) PCT Pub. No.: WO2007/076807
PCT Pub. Date: Jul. 12, 2007

(65) Prior Publication Data
US 2008/0306612 A1 Dec. 11, 2008

(30) Foreign Application Priority Data
Dec. 22, 2005 (DE) .......................... 10 2005 062 231

(51) Int. Cl.
*A61F 2/66* (2006.01)
(52) U.S. Cl. ................................ 623/55; 623/53; 623/47
(58) Field of Classification Search ................ 623/47–56
See application file for complete search history.

(56) References Cited

U.S. PATENT DOCUMENTS

| 1,289,580 | A | * | 12/1918 | Vincenti | 623/52 |
|---|---|---|---|---|---|
| 2,475,373 | A | | 7/1949 | Catranis | |
| 2,529,968 | A | | 11/1950 | Sartin | |
| 2,749,557 | A | | 6/1956 | Riddle | |
| 5,383,939 | A | * | 1/1995 | James | 623/24 |
| 5,913,902 | A | | 6/1999 | Geible | |
| 6,007,582 | A | * | 12/1999 | May | 623/55 |
| 6,602,295 | B1 | * | 8/2003 | Doddroe et al. | 623/55 |
| 6,669,737 | B2 | | 12/2003 | Mosler et al. | |
| 6,767,370 | B1 | | 7/2004 | Mosler et al. | |
| 7,520,904 | B2 | * | 4/2009 | Christensen | 623/47 |
| 2002/0013628 | A1 | | 1/2002 | Harris | |
| 2003/0045944 | A1 | | 3/2003 | Mosler et al. | |

(Continued)

FOREIGN PATENT DOCUMENTS

CN 1395479 A 2/2003

(Continued)

OTHER PUBLICATIONS

Machine Translation for DE10010302.*

(Continued)

*Primary Examiner* — William H. Matthews
*Assistant Examiner* — Marcia Hoffman
(74) *Attorney, Agent, or Firm* — Whitham Curtis Christofferson & Cook, PC

(57) ABSTRACT

The invention relates to an artificial foot with a connecting part for a lower leg part, a forefoot part which is pivotably connected to the connecting part by means of an upper coupling element and a lower coupling element in such a way that an angular position of the connecting part controls an angular position of the forefoot part, one of the coupling elements extending into a heel area of the foot.

10 Claims, 2 Drawing Sheets

U.S. PATENT DOCUMENTS

| | | | |
|---|---|---|---|
| 2004/0243253 A1* | 12/2004 | Cool et al. | 623/52 |
| 2005/0203640 A1* | 9/2005 | Christensen | 623/52 |
| 2008/0004718 A1 | 1/2008 | Mosler | |

FOREIGN PATENT DOCUMENTS

| | | |
|---|---|---|
| DE | 303735 | 3/1916 |
| DE | 309066 | 11/1917 |
| DE | 3232373 | 3/1983 |
| DE | 10010302 | 9/2001 |
| DE | 102004031562 | 2/2006 |
| FR | 486030 | 3/1918 |
| FR | 528796 | 11/1921 |
| GB | 2311466 | 3/1996 |
| TW | 371627 | 10/1999 |

OTHER PUBLICATIONS

Machine Translation for DE10010302 provided in 892 dated Jul. 9, 2010; Date for DE10010302: Sep. 20, 2001; Accessed: Jul. 1, 2010.*
International Search Report from PCT/DE2006/002241, 3 pgs, mailing date of May 31, 2007.

* cited by examiner

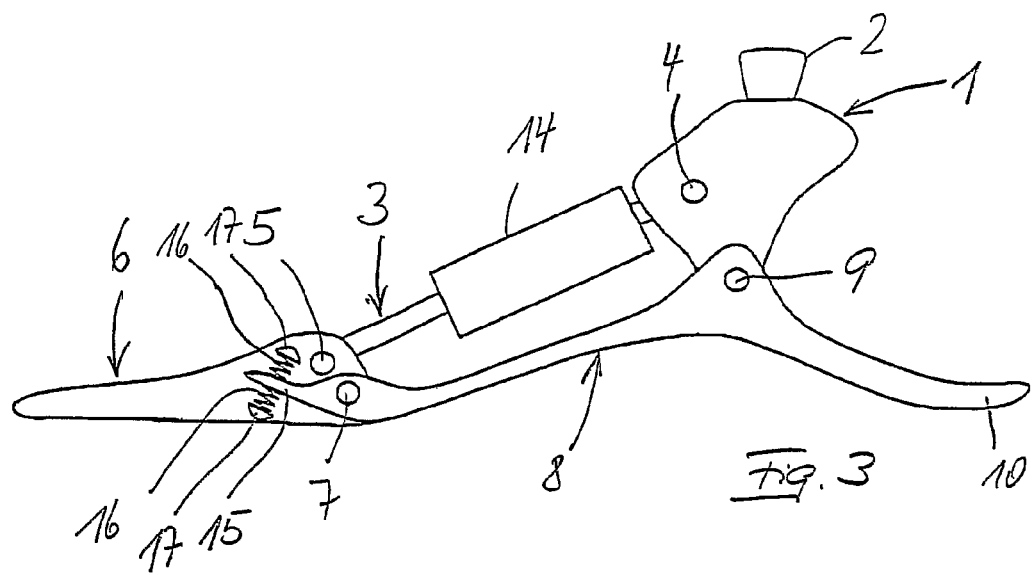
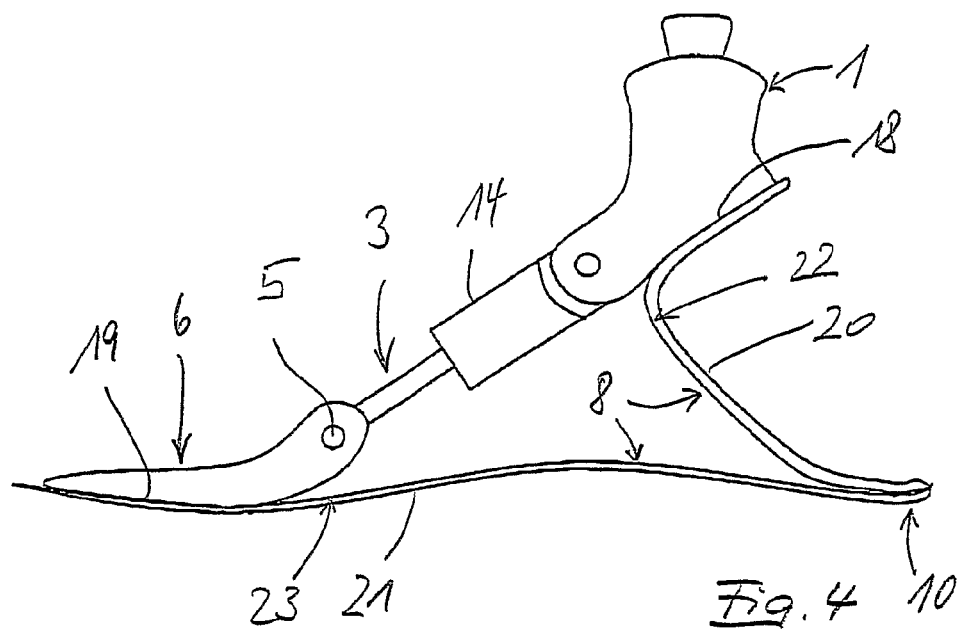

ARTIFICIAL FOOT

CROSS-REFERENCE TO RELATED APPLICATIONS

This application is a national stage application, filed pursuant to 35 U.S.C. §371, of PCT/DE2006/02241, filed Dec. 14, 2006, which claims priority to DE 10 2005 062 231.3 filed Dec. 22, 2006, which are hereby incorporated by reference in their entirety.

FIELD OF THE INVENTION

The invention relates to an artificial foot with a connecting part for a lower leg part, a forefoot part which is pivotably connected to the connecting part by an upper coupling element and a lower coupling element such that an angular position of the connecting part controls an angular position of the forefoot part. One of the coupling elements may extend into a heel area of the foot.

An artificial foot of is described in German patent application DE 10 2004 031 562 A1. By coupling a forefoot part of the artificial leg to a connecting part of the lower leg part via two coupling elements, a forced coupling between the connecting part and the forefoot part in respect of the angular position is achieved. A change in the angular position of the connecting part, or of the lower leg part, in the rearward direction leads to a proportional lifting of the forefoot part. The artificial foot, starting from a position without heel ("barefoot position"), can therefore be inserted into a shoe with a high heel, as a result of which the position of the lower leg, and thus of the connecting part, relative to the sole surface of the artificial foot changes by a rearward shifting of the angle. In this way, the forefoot part is lifted such that it again lies parallel to the contact surface (front sole of the shoe). The forefoot part therefore lies firmly on the supporting surface and takes up the required load for a secure stance, even with the high heel. A soft or elastic design of the forefoot part, is therefore not needed.

The above-described artificial foot preferably contains a multiple-joint arrangement, in particular a four-joint arrangement, in which the coupling elements between the forefoot and a midfoot area can lie substantially parallel to each other. This results in a 1:1 coupling of the angle movements of connecting part and forefoot part, which is ideal for heel height adaptation. In the above-described artificial foot, the upper coupling element extends into the heel area and is thus designed as a kind of rocker which is articulated more or less centrally on the connecting part. This construction has the advantage that the pivot joint of the upper coupling member is arranged approximately in the position of the natural ankle joint. A disadvantage, however, is that the loading movement of the rocker-type upper coupling element changes the length of the artificial foot in the sole area, such that unwanted wandering of the foot may occur, for example, in the case of a rocking load.

An object of the present invention is to achieve the advantages of an artificial foot of the type described above without having changing the length of the foot caused by the movement of the upper coupling member.

According to one embodiment of the invention, an artificial foot of the type described above includes a lower coupling element that extends into the heel area, such that the movement of the forefoot part attached to the lower coupling element does not change the length of the foot. The position of the lower coupling member joint is critical to ankle movement. Accordingly, the joint of the lower coupling member according to one embodiment lies slightly below the position of the physiological ankle joint, since, for cosmetic reasons, an appreciably higher foot construction is undesirable.

The artificial foot according to embodiments of the invention permits automatic adaptation of the angular position of the forefoot part with respect to the rest of the contact surface of the sole of the artificial foot. This surface is defined by the "ball" at the connection point between the forefoot part and the coupling elements forming the midfoot area, and the "heel" at the rear end of the heel area. In a shoe with a high heel, this contact surface is oblique with respect to the horizontal. Since the lower leg must be oriented substantially vertically in order to retain equilibrium, this results in a rearwardly shifted angle between the lower coupling element and the connecting part for the lower leg part. This angle is transferred to the forefoot part and ensures lifting of the forefoot part, such that the latter is oriented parallel to the ground or to the front sole area of a shoe and can then take up forces in the forefoot area, thus giving a high degree of stability of stance.

As in the construction described above according to DE 10 2004 031 562 A1, one of the coupling elements may be designed to be adjustable in length within certain limits. For walking, a direct transfer of the angular position of the ankle to the forefoot part may not be advantageous. Instead, transfer is caused by an oblique positioning of the coupling elements, which converts the angle movements of the ankle into corresponding movements of the forefoot part. In this case, adjusting the length of one of the coupling members is sufficient to compensate for the heel height. This can be done statically, such that a length adjustment takes place only when the shoe is changed to adapt to the heel height. However, a dynamic change of length is also possible, by one of the coupling elements being able to lengthen elastically or, for example, being adjusted in length by a hydraulic cylinder.

In this way, it is possible to lessen the strong loading of the forefoot part when weight is shifted forward. If the change in length occurs against the action of an increasing elastic counter-force, a progressively increasing counter-force of the forefoot results. A certain degree of "swaying" of the patient when standing is thus stabilized with an elastic and progressively increasing counter-force, which corresponds to the feel of a natural stance.

The change in length of the coupling elements can also be caused by a hydraulic cylinder, for example, by a hydraulic cylinder that is adjustable only by small changes and that blocks in the event of abrupt loads. Such a hydraulic cylinder is explained in detail in DE 10 2004 031 562 A1.

For the dynamics of walking, it is advantageous if the relative movement between the heel area and the coupling element is attenuated by a damper arrangement. The damper arrangement should have a damping spring function, but it may also be designed to react to static loads by providing a hydraulic cylinder with a bypass opening. In this way, the adaptation to different heel heights achieved such that the respective standing position is free of forces and does not have to be maintained against any counter-force.

In an alternate embodiment the articulated connection of the coupling elements is a resilient link. The resilient link can be provided at one or both ends of the coupling element.

In a particular embodiment of the invention, the lower coupling element bears resiliently on the forefoot part and on the connecting part in each case via a leaf spring element, and the two leaf spring elements are guided into the heel area where their surfaces bear on each other. The leaf spring element that is joined to the connecting element forms a C-shape, whereas the leaf spring element that is joined to the forefoot part has a slight undulating shape.

The artificial foot according to the invention is also suitable for an additional dynamic adjustment in which the damping properties of one coupling element can be continuously controlled, for example, in the case of a hydraulic cylinder, with an electronically adjustable valve. The control can take place as a function of measured loading states and positional states of the foot.

The present invention will be explained in more detail below on the basis of illustrative embodiments depicted in the drawing, in which:

FIG. 3 shows a second embodiment of the artificial foot according to the invention;

FIG. 4 shows a third embodiment of the artificial foot according to the invention.

Figure 1:
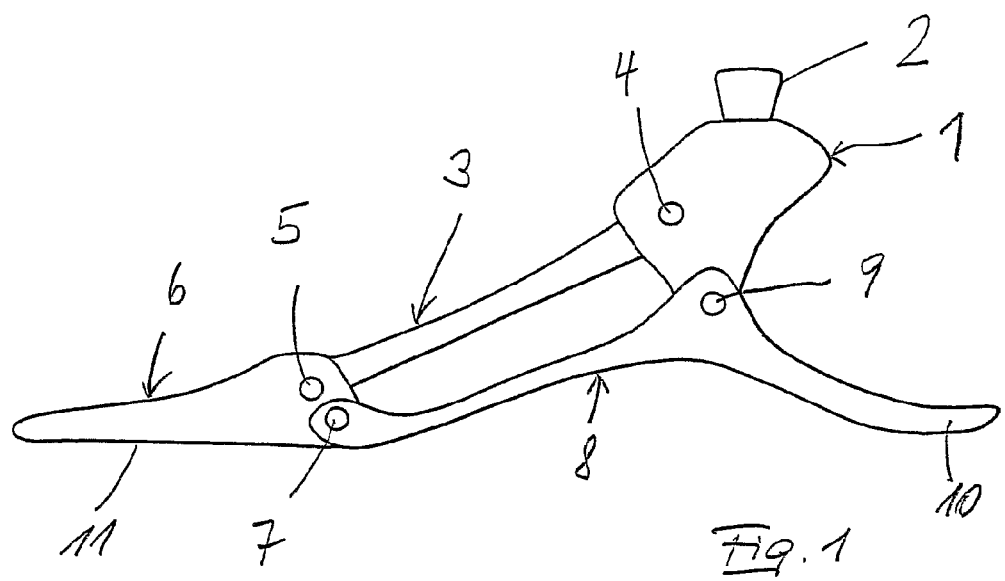
FIG. 1 shows a side view of a first illustrative embodiment of an artificial foot according to the invention.

A first embodiment of a foot according to the invention, as shown in FIG. 1, has a connecting part 1 which, on its top, is provided with an adapter attachment 2 in the form of an upturned truncated cone or pyramid. The adapter attachment 2 allows a tubular lower leg part of a below-knee prosthesis to be adjustably received.

An upper coupling element 3 is connected at one end to the connecting part 1 by a pivot joint 4. The other end of the upper coupling element 3 is connected to a forefoot part 6, which simulates the toe area of a natural foot, by a pivot joint 5. A lower coupling element 8 is connected at one to the forefoot part 6 via a pivot joint 7 below the pivot joint 5. The lower coupling element 8 is connected at the other end to the connecting part 1 via a pivot joint 9 positioned on a lower end of the connecting part 1. The coupling element 8 extends past the pivot joint 9 and into a free heel end 10 such that it protrudes into a heel area of the foot. The free heel end 10 is angled slightly downward. The lower coupling element 8, with its rear free heel end 10 and the two pivot joints 7, 9, forms a rocker which, for example when the foot is set down on the heel to take a step, is loaded by a ground resistance force at the free heel end 10. This exerts a torque on the forefoot part 6, causing the forefoot part 6 to pivot upward. In this manner, the pivot joint 9 of the rocker corresponds to the ankle joint.

The forefoot part 6 forms an approximately triangular wedge with an underside 11 that lies parallel to a ground surface (not shown) for the foot in the area of the forefoot part 6.

Figure 2:
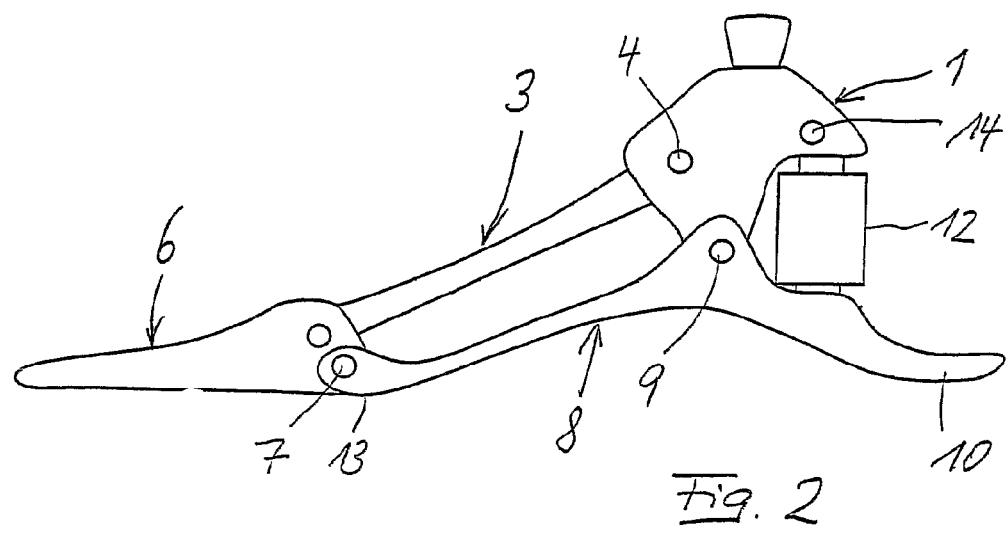
FIG. 2 shows a side view of the modified first embodiment.

In the illustrative embodiment shown in FIG. 1, the connecting part 1, the coupling elements 3, 8 and the forefoot part 6 are rigid. A load in the area of the heel end 10 thus causes the forefoot part 6 to turn upward, which corresponds to a lifting of the toes of a natural foot. To attenuate this unnatural movement, the embodiment according to FIG. 2 includes a damper 12 which is arranged between the connecting part 1 and the heel end 10 of the lower coupling element 8. When a ground reaction force acts on the heel end 10, the damper 12 causes a delayed and, if appropriate, limited upward pivot of the rear heel end 10, resulting in a correspondingly delayed and limited upward pivot of the forefoot part 6.

In one embodiment, the damper 12 is a hydraulic cylinder with a bypass opening which is closed if the flow speed is too great. In this way, the angular position between the connecting part 1 and the rear heel end 10 or the lower coupling element 8 may be altered statically, for example if the artificial foot is inserted into a shoe with a high heel. In this way, it is possible to adapt the angular position of the connecting part 1, and thus of the lower leg part of a prosthesis, relative to the lower coupling element 8. Accordingly, if the lower coupling element 8 extends away as a result of a high heel, a vertical orientation of the lower leg part is permitted, which does not have to be maintained against elastic restoring forces.

The angular position of the lower coupling element 8 also results from the bearing surfaces at the rear heel end 10 and at the front ball end 13 provided with the pivot joint 7.

The damper 12 is likewise connected in an articulated manner to the rear heel end 10 and to the connecting part 1. A corresponding pivot joint 14 in the connecting part 1 can be seen in FIG. 2.

In the illustrative embodiment shown in FIG. 3, the upper coupling element 3 is adjustable in length by a hydraulic cylinder 14. This embodiment contributes to adapting the artificial foot to different heel heights of a shoe. Moreover, the lower coupling element 8 includes an extension piece 15 which continues the lower coupling element 8 past the pivot joint 7 into a free end, which on both sides acts on a compression spring 16, which interacts with a stationary limit stop 17. The pivoting of the lower coupling element 8 relative to the forefoot part 6 is elastically damped by the compression springs 16 and limited by the limit stops 17, so as to avoid excessive pivoting of the forefoot part 6.

In another embodiment of a foot according to the invention as shown in FIG. 4, the connecting part 1 and the forefoot part 6 each include a contact face 18, 19 on which a corresponding portion of a respective leaf spring element 20, 21 is secured and bears thereon. The two leaf spring elements 20, 21 together form the lower coupling element 8, which is elastic. The leaf spring element 20 is joined to the connecting part 1, is approximately C-shaped and embodies a resilient heel element, thereby performing a function similar to the damper 12 in FIG. 2. The leaf spring element 21 is connected to the forefoot part 6 and extends similar to a sole, as an undulating shape from the forefoot part 6 to the heel end 10. At the heel end 10 both leaf spring elements 20, 21 bear flat on each other, are connected to each other, and together form a free end.

The configuration of the leaf spring elements 20, 21 results in pivot points 22, 23. The pivot point 22 lies near the connecting part 1 and performs the ankle-joint function, while the pivot point 23 on the leaf spring element 21 lies in the area of the ball of the artificial foot.

It will be noted that, in the embodiments shown in FIGS. 1 to 4, the pivoting angle of the forefoot part 6 is controlled without changing the effective length of the foot.

The invention claimed is:

1. An artificial foot comprising:
a connecting part configured for connection to a lower leg part;
a forefoot part;
an upper coupling element pivotably connecting the connecting part and the forefoot part by means of first and second pivot joints, respectively; and
a lower coupling element pivotably connecting the connecting part and the forefoot part by means of third and fourth pivot joints, respectively, such that throughout a walking process an angular position of the connecting part continuously controls an angular position of the forefoot part, whereby coupling of the forefoot part to the connecting part consists of a four-joint arrangement composed of said first and second pivot joints and said third and fourth pivot joints,
wherein the lower coupling element extends from the forefoot part and past the connecting part to define a heel end of the artificial foot and wherein the lower coupling element is pivotably connected to the connecting part at the third pivot joint and is pivotably connected to the forefoot part at the fourth pivot joint located below the second pivot joint such that upon the application of a ground resistance force on the heel end, the lower coupling element exerts a torque on the forefoot part and causes the forefoot part to pivot upward, wherein one of the coupling elements is adjustable in length.

2. The artificial foot as claimed in claim 1, wherein the length-adjustable coupling element is adjustable against an increasing elastic counter-force.

3. The artificial foot as claimed in claim 1, wherein the length-adjustable coupling element includes a hydraulic cylinder.

4. The artificial foot as claimed in claim 1, wherein the upper coupling element is adjustable in length.

5. The artificial foot as claimed in claim 1, wherein a damper arrangement is positioned between the connecting part and the heel end.

6. The artificial foot as claimed in claim 1, wherein the lower coupling element bears resiliently on the forefoot part and the connecting part.

7. The artificial foot as claimed in claim 1, wherein the movement of the forefoot part relative to the lower coupling element is limited by a resilient stop device interposed between the forefoot portion and the lower coupling element.

8. The artificial foot as claimed in claim 1, wherein a damping property of the upper or lower coupling element is adjustable as a function of measured loading states or positional states of the foot.

9. An artificial foot comprising:
a connecting part configured for connection to a lower leg part;
a forefoot part;
an upper coupling element pivotably connecting the connecting part and the forefoot part by first and second pivot joints, respectively; and
a lower coupling element pivotably connecting the connecting part and the forefoot part by means of first and second pivot points, respectively, such that throughout a walking process an angular position of the connecting part continuously controls an angular position of the forefoot part, whereby coupling of the forefoot part to the connecting part consists of a four-joint arrangement composed of said first and second pivot joints and said first and second pivot points,
wherein the lower coupling element comprises two leaf spring elements connected to each other to define a heel end of the artificial foot, one spring element which is connected to the forefoot part and the other spring element which is connected to the connecting part, the configuration of the leaf spring elements resulting in the first and second pivot points, the first pivot point lying near the connecting part and performing an ankle-point function, and the second pivot point lying in an area of a ball of the artificial foot adjacent the forefoot part.

10. An artificial foot comprising:
a connecting part configured for connection to a lower leg part;
a forefoot part;
an upper coupling element pivotably connecting the connecting part and the forefoot part by means of first and second pivot joints, respectively; and
a lower coupling element pivotably connecting the connecting part and the forefoot part by means of third and fourth pivot joints, respectively, such that throughout a walking process an angular position of the connecting part continuously controls an angular position of the forefoot part, whereby coupling of the forefoot part to the connecting part consists of a four-joint arrangement composed of said first and second pivot joints and said third and fourth pivot joints,
wherein the lower coupling element extends from the forefoot part and past the connecting part to define a heel end of the artificial foot and wherein the lower coupling element is pivotably connected to the connecting part at the third pivot joint and is pivotably connected to the forefoot part at the fourth pivot joint located below the second pivot joint such that upon the application of a ground resistance force on the heel end, the lower coupling element exerts a torque on the forefoot part and causes the forefoot part to pivot upward,
wherein a damping property of the upper or lower coupling element is adjustable as a function of measured loading states or positional states of the foot.

* * * * *